(12) United States Patent
Fabinski et al.

(10) Patent No.: US 6,493,087 B1
(45) Date of Patent: Dec. 10, 2002

(54) METHOD FOR MEASURING NOX

(75) Inventors: Walter Fabinski, Kriftel (DE); Michael Zöchbauer, Oberursel (DE); Michael Moede, Neu Anspach (DE)

(73) Assignee: ABB Patent GmbH, Mannheim (DE)

( * ) Notice: Subject to any disclaimer, the term of this patent is extended or adjusted under 35 U.S.C. 154(b) by 0 days.

(21) Appl. No.: 09/915,013

(22) Filed: Jul. 25, 2001

(30) Foreign Application Priority Data

Jul. 28, 2000 (DE) .......................................... 100 36 948

(51) Int. Cl.⁷ ................................................ G01N 15/02
(52) U.S. Cl. ........................................ 356/437; 235/439
(58) Field of Search ................... 356/437, 439

(56) References Cited

U.S. PATENT DOCUMENTS 5,621,213 A * 4/1997 Barshad ...................... 356/437

* cited by examiner

Primary Examiner—Harold I. Pitts
(74) Attorney, Agent, or Firm—Michael M. Rickin, Esq.

(57) ABSTRACT

A method for measuring NOx having a specific discharge lamp. The method controls a photometric analysis device, in which an electrically rotatable filter wheel or shutter wheel is used to change various shutters and/or filters in a beam path with beam source, cuvette and detector. The filter and/or shutter wheel is controlled in such a way that the measurement time is greater than the transfer time. This control improves the detection limit of the NOx resonance absorption method.

12 Claims, 2 Drawing Sheets

METHOD FOR MEASURING NOX

FIELD OF THE INVENTION

This invention relates to a method for measuring NOx and more particularly to the NO resonance absorption method for measuring NOx.

DESCRIPTION OF THE PRIOR ART

The brochure CLD 70E/February 1997 produced by ECO-Physics discloses an analysis unit for measuring low NO concentrations which uses the chemiluminescence method (CLD). However, the equipment associated with this method has a number of drawbacks.

Firstly, an ozone generator is required in order to produce the ozone which is required for the chemiluminescence reaction. Ozone is highly toxic and a relatively high outlay is required in order to prevent ozone from escaping from the equipment. For example, an ozone annihilator is required to be arranged at the measurement gas outlet.

Secondly, the CLD method requires a vacuum pump with pressure regulation. A drawback of this is that the vacuum pump is susceptible to faults and involves high maintenance. A further drawback is the relatively high production costs of the CLD equipment.

A further brochure, produced by ABB Analytical, has disclosed the FTIR method, which can be used to detect low NO concentrations. In this case too, a relatively high outlay on equipment has to be incurred. Firstly, a long-path absorption cell has to be used in order to achieve the high measurement sensitivity. At the same time, the high volume of this cell prevents, for example, the rapid measurement which is desired when carrying out measurements in automotive exhaust gas. Secondly, chemical measurement calculations are required in order to suppress interfering cross-sensitivities. These calculations are complex and likewise hinder rapid measurement.

Finally, DE 2541162 has disclosed the photometric nitrogen oxide resonance absorption method. Although this method is simple to carry out and is highly selective for nitrogen oxide, the measurement sensitivity which has been achieved to date is insufficient to detect very low NO concentrations. Hitherto, this technique has employed a modulation method in which a uniformly revolving filter wheel produces a measurement phase and a comparison phase.

The actual measurement time in the measurement and comparison phases is relatively short with respect to the revolution time of the filter wheel. The unfavorable time ratio means that the optimum signal-to-noise ratio which is required is not produced and therefore nor is the optimum measurement sensitivity. Therefore it is desirable to increase the measurement sensitivity of the NO resonance absorption method.

SUMMARY OF THE INVENTION

In a device for measuring NOx having a specific discharge lamp as a beam source and a cuvette and a detector in a beam path from the beam source, an electrically rotatable filter wheel or shutter wheel to change various shutters or filters in a beam path from the beam source, a cuvette and a detector, a method for measuring NOx comprising the steps of:

(a) using an electronically rotatable filter wheel or shutter wheel in the beam path between the cuvette and the detector to change various shutters and filters between measurement and comparison phases; and (b) controlling the filter wheel or shutter wheel to make the measurement time of the detector greater than the transfer time of the detector.

A device for measuring NOx comprising:

a. a specific discharge lamp as a beam source;

b. a cuvette and a detector in a beam path from the beam source;

c. an electrically rotatable filter wheel or shutter wheel for changing various filters or shutters in the beam path between the cuvette and the detector wherein the rotation of the filter wheel or the shutter wheel takes place in steps such that the measurement time of the detector is greater than the transfer time of the detector.

In a device for measuring NOx having a specific discharge lamp as a beam source and a cuvette and a detector in a beam path from the beam source, an electrically rotatable filter wheel or shutter wheel to change various shutters or filters in a beam path from the beam source, a cuvette and a detector, a method for measuring NOx comprising the steps of:

(a) using an electronically rotatable filter wheel or shutter wheel in the beam path between the cuvette and the detector to change various shutters and filters between measurement and comparison phases;

(b) controlling the filter wheel or shutter wheel by a stepper motor having a step width to make the measurement time of the detector greater than the transfer time of the detector; and (c) determining the step width so that the position of the filter wheel or shutter wheel can be transferred directly between the measurement and comparison phases.

DESCRIPTION OF THE PREFERRED EMBODIMENT(S)

Figure 1:
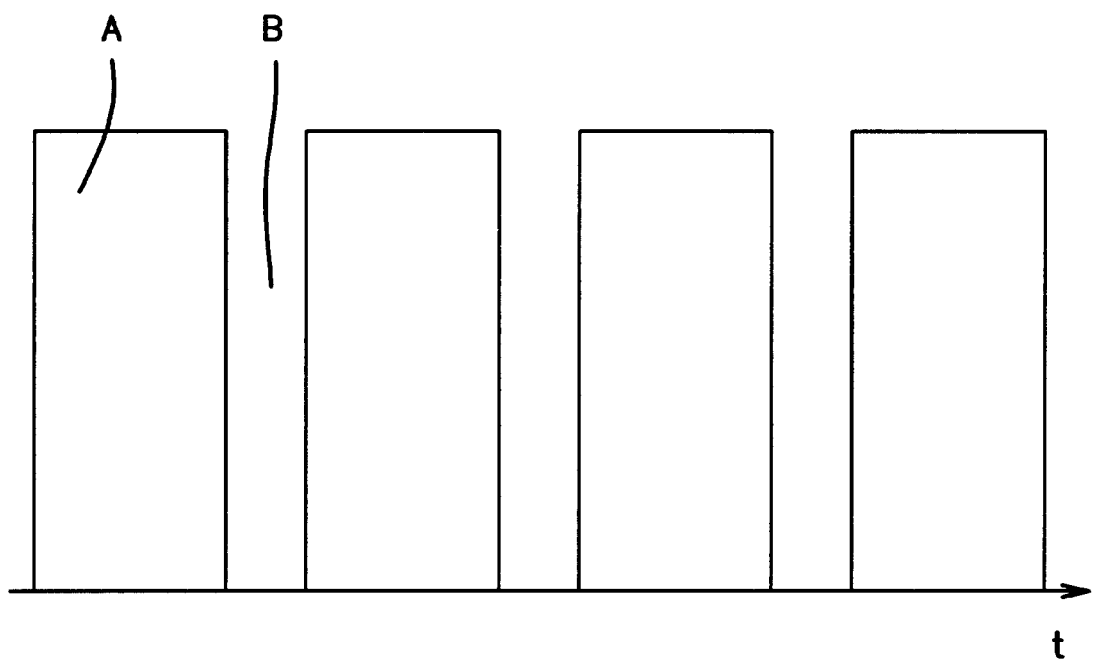
FIG. 1 shows the ratio of transfer time to measurement time in the method according to the invention.
Figure 3:
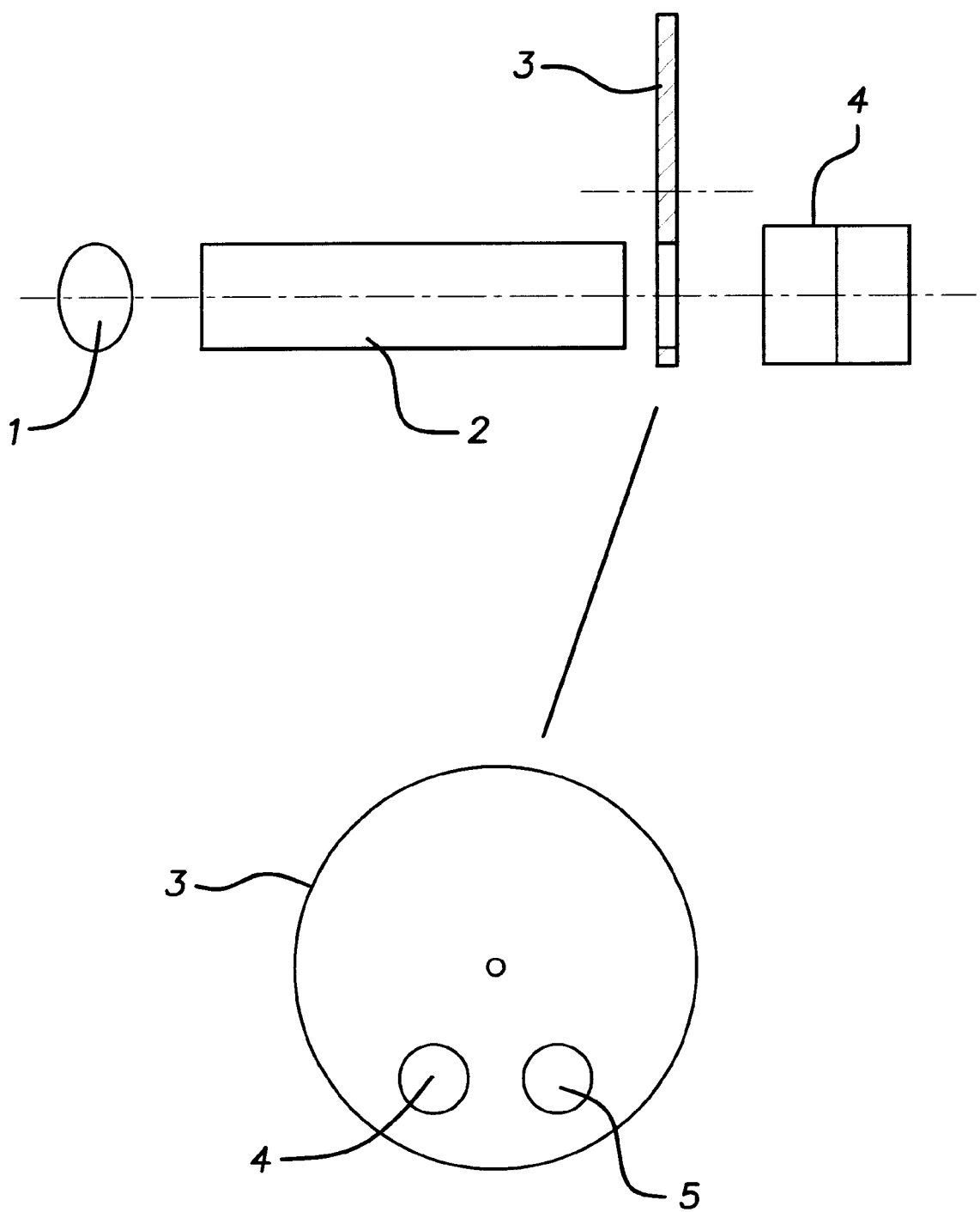
FIG. 3 shows a shutter wheel.

Referring now to FIG. 1 there is shown the measurement times A and the transfer times B between the measurement times, during which, by stepwise rotation of the shutter wheel 3 shown in FIG. 3, the filters or shutters 4 and 5 of FIG. 3 are successively pivoted into the beam path. The beam path is, however, is not shown in more detail in FIG. 1 since it is otherwise known. A basic outline of the beam path is shown in FIG. 3.

Figure 2:
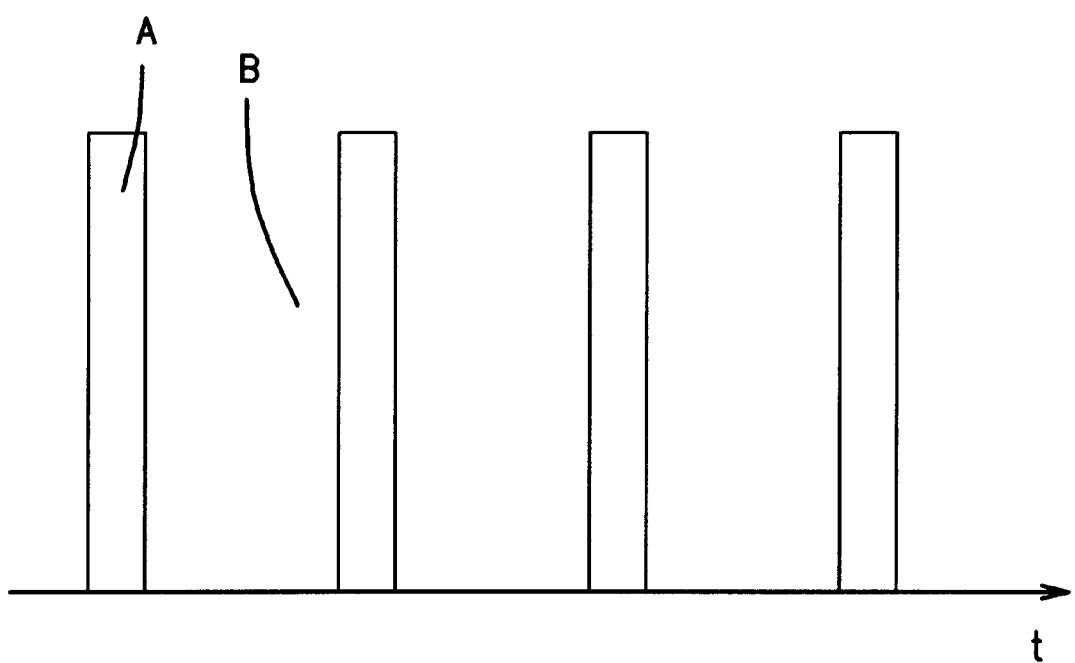
FIG. 2 shows the ratio of transfer time to measurement time in the prior art.

It can be seen from FIG. 1 that the measurement times A, are significantly greater compared to the illustration of the prior art transfer to measurement times shown in FIG. 2, and in fact are even greater by a multiple, than the transfer times B. In this way, it is possible to drastically increase the measurement signal-to-noise ratio. This makes it possible to detect extremely low concentrations, in particular low NOx concentrations. For example, in the present case, the signal-to-noise ratio is improved by a factor of $10^{0.5}$, i.e. by a factor of about 3.

One possibility for implementing the invention consists in dispensing with uniform rotation of the filter wheel 3 and instead controlling the filter wheel 3 using a stepper motor (not shown in FIG. 3). The stepwise control enables the measurement time to be lengthened in a controlled way and the transfer time to be reduced in a controlled way. Another possible option consists in arranging measurement and comparison phases of the filter wheel 3 close together, in order in this way to minimize the transfer time.

FIG. 2 shows a typical measurement/transfer profile in a method according to the prior art. In this case, the measurement times A are short and the transfer times B are long. By contrast, in accordance with FIG. 1, however, the drastic improvement which has already been mentioned above is achieved by the method according to the invention.

FIG. 3 shows a shutter wheel 3 in which the filters or shutters 4 and 5 for the measurement and comparison phases are arranged directly adjacent to one another, which produces or promotes the short transfer time according to the invention. Apart from this, the beam path comprises a beam source 1, a cuvette 2, the shutter wheel 3, part of which is also shown in detail in this figure, and a detector 4.

The shutter wheel 3 is controlled by a stepper motor (not shown). This makes it possible in a simple way to achieve the minimal transfer times in conjunction with the shutters or filters being arranged directly adjacent to one another, leading to the inventive effect which has been described.

It is to be understood that the description of the preferred embodiment(s) is (are) intended to be only illustrative, rather than exhaustive, of the present invention. Those of ordinary skill will be able to make certain additions, deletions, and/or modifications to the embodiment(s) of the disclosed subject matter without departing from the spirit of the invention or its scope, as defined by the appended claims.

What is claimed is:

1. In a device for measuring NOx having a specific discharge lamp as a beam source and a cuvette and a detector in a beam path from said beam source, an electrically rotatable filter wheel or shutter wheel to change various shutters or filters in a beam path from said beam source, a cuvette and a detector, a method for measuring NOx comprising the steps of:

(a) using an electronically rotatable filter wheel or shutter wheel in said beam path between said cuvette and said detector to change various shutters and filters between measurement and comparison phases; and (b) controlling said filter wheel or shutter wheel to make the measurement time of said detector greater than the transfer time of said detector.

2. The method of claim 1 wherein said measurement time is greater than said transfer time by a multiple.

3. The method of claim 1 wherein said filter wheel or shutter wheel is controlled by a stepper motor and the step width of said stepper motor is determined in such a way that the position of said filter wheel or shutter wheel can be transferred directly between said measurement and said comparison phases..

4. The method of claim 2 wherein said filter wheel or shutter wheel is controlled by a stepper motor and the step width of said stepper motor is determined in such a way that the position of said filter wheel or shutter wheel can be transferred directly between said measurement and said comparison phases.

5. The method of claim 3 wherein said filters or shutters on said filter wheel or said shutter wheel are arranged directly adjacent to one another and said step width is adapted accordingly or minimized.

6. The method of claim 4 wherein said filters or shutters on said filter wheel or said shutter wheel are arranged directly adjacent to one another and said step width is adapted accordingly or minimized.

7. A device for measuring NOx comprising:

a. a specific discharge lamp as a beam source;

b. a cuvette and a detector in a beam path from said beam source;

c. an electrically rotatable filter wheel or shutter wheel for changing various filters or shutters in said beam path between said cuvette and said detector wherein the rotation of said filter wheel or said shutter wheel takes place in steps such that the measurement time of said detector is greater than the transfer time of said detector.

8. The device of claim 7 wherein said filters or shutters are arranged directly adjacent to one another on said filter wheel or said shutter wheel.

9. In a device for measuring NOx having a specific discharge lamp as a beam source and a cuvette and a detector in a beam path from said beam source, an electrically rotatable filter wheel or shutter wheel to change various shutters or filters in a beam path from said beam source, a cuvette and a detector, a method for measuring NOx comprising the steps of:

(a) using an electronically rotatable filter wheel or shutter wheel in said beam path between said cuvette and said detector to change various shutters and filters between measurement and comparison phases;

(b) controlling said filter wheel or shutter wheel by a stepper motor having a step width to make the measurement time of said detector greater than the transfer time of said detector; and (c) determining said step width so that the position of said filter wheel or shutter wheel can be transferred directly between said measurement and said comparison phases.

10. The method of claim 9 wherein said measurement time is greater than said transfer time by a multiple.

11. The method of claim 9 wherein said filters or shutters on said filter wheel or said shutter wheel are arranged directly adjacent to one another and said step width is adapted accordingly or minimized.

12. The method of claim 10 wherein said filters or shutters on said filter wheel or said shutter wheel are arranged directly adjacent to one another and said step width is adapted accordingly or minimized.

\* \* \* \* \*